United States Patent [19]

Liang

[11] Patent Number: 5,414,258

[45] Date of Patent: May 9, 1995

[54] APPARATUS AND METHOD FOR CALIBRATION OF FLUORESCENCE DETECTORS

[75] Inventor: Louis H. Liang, Los Altos, Calif.

[73] Assignee: Angstrom Technologies, Inc., Florence, Ky.

[21] Appl. No.: 156,249

[22] Filed: Nov. 22, 1993

[51] Int. Cl.$^6$ ............................................. G01N 21/64
[52] U.S. Cl. .............................. 250/252.1; 250/458.1; 356/243
[58] Field of Search ...................... 250/252.1 A, 522.1, 250/458.1, 271, 483.1, 486.1, 459.1; 356/243

[56] References Cited

U.S. PATENT DOCUMENTS

| | | | |
|---|---|---|---|
| 4,302,678 | 11/1981 | Schiffert | 250/252.1 A |
| 4,662,745 | 5/1987 | Zupanick et al. | 250/252.1 A |
| 5,089,709 | 2/1992 | Chadwick | 250/458.1 |
| 5,093,234 | 3/1992 | Schwartz | 435/7.21 |
| 5,125,747 | 6/1992 | Sayegh et al. | 356/407 |

OTHER PUBLICATIONS

West et al., "Practical Standards for UV Absorption and Fluorescence Spectrophotometry—Developments in Photophysical Instrumentation Part 3", American Laboratory, 9(3), Mar. 1977, pp. 37–52.

*Primary Examiner*—Carolyn E. Fields
*Attorney, Agent, or Firm*—Theodore Touw

[57] ABSTRACT

The response of a fluorescence detector is calibrated using apparatus and methods for both static and dynamic calibrations. The apparatus and methods are especially suited for portable use in field calibration of fluorescence detectors of authentication systems that use non-visible light. The calibration apparatus incorporates standard target elements (20) comprising predetermined fluorescent substances with known emission spectra, and either non-fluorescent substances or fluorescent substances with other known emission spectra. The substances are either mixed in predetermined proportions, or one substance is arranged in a predetermined pattern (170), such as a bar code, on the other substances. An aperture (30) exposes a predetermined surface area of a standard target element to the view of the fluorescence detector. The distance of the standard target element from the optical front end (70) of the fluorescence detector to be calibrated is adjustable (50). For dynamic calibration, the standard target element is moved from one position to another in the apparatus in a predetermined time. Multiple standard target elements are substituted individually into the apparatus or are carried together on a carrier (80) that is indexed to present each standard target element in turn. Additional light can be admitted to the apparatus through a port (200) to simulate the ambient light encountered in normal use of the fluorescence detector. Standardized quick-disconnect couplings (220, 230) provide for easy exchange of the calibration apparatus among various fluorescence detectors.

34 Claims, 4 Drawing Sheets

APPARATUS AND METHOD FOR CALIBRATION OF FLUORESCENCE DETECTORS

FIELD OF THE INVENTION

In many applications, it is desirable to precisely and reproducibly calibrate apparatus for detecting fluorescent radiation excited by non-visible light, such as ultraviolet (UV) light. Such apparatus may be used, for example, to authenticate articles such as passports, legal documents, manufactured articles of high value, etc. previously marked with fluorescent substances. The need to calibrate such apparatus is required by both manufacturers and users of UV-excited scanners, readers, bar-code readers, and optical character recognition scanners, for example. The need for reproducible calibration is particularly important for low-level signal detection, wavelength-specific applications, and fine resolution image applications of fluorescent radiation.

It is particularly important in the use of authentication systems that they be calibrated accurately. If their calibration were inaccurate in one direction, authentic articles could be mis-identified as counterfeit. If their calibration were inaccurate in the opposite direction, counterfeit articles could be accepted as authentic. It is also desirable to have calibration standards such that all detectors of a given type can be set up uniformly, so that their responses to the same stimuli will be substantially equal. The standards used for such calibrations should further be rugged, small, inexpensive, and easy-to-use, particularly for use in the field. It is an object of this invention to provide calibration standards apparatus and methods satisfying all these needs, particularly for fluorescence detectors used in authentication systems.

BACKGROUND

Fluorescence detecting apparatus is commonly used in the fields of analytical chemistry and cytometry, and for those applications, methods of calibration are well developed and well-known to those skilled in those fields. For example U.S. Pat. Nos. 5,093,234 and 4,868,126 and many other patents and publications disclose methods of calibrating flow cytometers and fluorescence microscopes. The apparatus and method of the present invention is not particularly suited to these fields of scientific analysis.

The field of application of the present invention relates particularly to the uses of fluorescence detection in the authentication of genuine articles and in the detection of counterfeit articles, and to the uses of similar apparatus in process control and quality control.

The counterfeiting of documents such as passports, customs and immigration documents, identification cards, driver's licenses, and credit cards has become a problem that is costly to the public in many ways. When such documents are used by unauthorized persons, such use often results in direct financial losses to the public and in indirect losses due to increased cost of law enforcement and increased cost of insurance against losses. Similar problems and costs to the public occur as a result of counterfeiting or "pirating" of brandname products by unauthorized manufacturers and by copyright infringers.

Some of the systems that have been developed to prevent these problems have used marking with fluorescent substances to identify authentic articles, and such systems have used non-visible radiation to excite the fluorescent substances to confirm the identity of authentic articles or to reveal counterfeit articles which lack the predetermined fluorescent markings. Some systems using fluorescent markings depend on quantitative measurements of quantifiable characteristics of the fluorescent radiation, such as the intensity, wavelength or spatial distribution of the fluorescent markings. An example of such a system is disclosed in U.S. Pat. No. 4,642,526 (Hopkins, 1987). It is these systems and similar systems described below to which the present invention is directed.

The same apparatus that is used for authentication of articles can also be used in quality control and in process control of manufacturing processes. In those applications, the presence or absence of a required substance or the amount of such a substance is determined by tagging the required substance with a fluorescent substance and by using a fluorescence detector to measure the tagged combination. The calibration of systems used for these purposes can also be accomplished easily with the present invention.

SUMMARY OF THE INVENTION

The calibration standard apparatus of this invention has a housing adapted to fit the optical front end of a fluorescence detecting system using non-visible light. The housing encloses a fluorescent standard target element, an aperture, and a focal distance adjustment mechanism. In embodiments intended to calibrate apparatus for applications requiring relative movement (such as bar-code readers), the fluorescent standard target element is moved by an actuator mechanism contained wholly or partly within the housing. Thus the invention is useful for both static and dynamic calibrations. In some embodiments of the invention, the housing has provision for introduction of additional light to simulate during calibration the ambient light environment in which the fluorescence detector is to be used. That provision for introducing light can be a fiber-optic input port.

In the remainder of this document, the term "standard" by itself will be used to refer to the entire calibration standard apparatus, and the term "standard target element" will be used to refer specifically to a discrete portion of the apparatus prepared with a predetermined amount of fluorescent substance incorporated in it in a predetermined manner.

The fluorescent standard target element itself may be a solid, liquid, or gaseous material and may be encapsulated in a protective container or coating transparent to both the non-visible exciting radiation and the fluorescent radiation. The material contained within the fluorescent standard target element may be a predetermined mixture or solution containing one or more target fluorescent substances in a matrix material. The matrix material may be non-fluorescent or may itself be fluorescent with a fluorescent emission spectrum different from the target fluorescent substance for which the apparatus is to be calibrated. A simple example of such a standard target element is a plastic disk molded from an inert non-fluorescent plastic into which is mixed a predetermined percentage of a fluorescent substance for which the fluorescence detector is to be calibrated.

In the standard target element, the fluorescent substance may be arranged in a pattern such as a bar code pattern, against a non-fluorescent background. Such a pattern may be reversed, i.e. a non-fluorescent substance may be arranged in a pattern on a fluorescent background. The pattern may be a fine line of fluorescent material on a non-fluorescent background, or a predetermined image, or any spatial arrangement of fluorescent and non-fluorescent substances as required for particular applications.

In a preferred embodiment, the transparent material of the standard target element container or coating is quartz. In another embodiment, the coating material is a plastic material extruded or molded over at least the portion of the standard target element containing fluorescent substances. Other materials transparent both to the fluorescent radiation and to the radiation used to excite it can be used in alternate embodiments. It is clear that not all standard target elements require the protection of a transparent container or coating. Some materials are sufficiently inert and mechanically robust so that they do not require a coating or container. For example such robust materials include some molded or extruded plastic materials containing the fluorescent substance for which detectors are to be calibrated.

The calibration standard may be used with a number of different fluorescence detector systems having different physical configurations, including different size optical front ends, such as various sizes of lens housings or of optical fiber connectors. Standardized adapters are used in preferred embodiments of the invention to adapt a number of different standard target elements to a particular type of authentication system, or conversely to adapt a particular standard target element or set of such elements to a number of authentication systems having optical front ends that differ from each other. A preferred standard adapter is a bayonet-type adapter such as those commonly used for connecting camera lenses to cameras.

Thus the invention is especially useful for portable use in field calibration of fluorescence detectors of authentication systems that use non-visible light.

DETAILED DESCRIPTION OF THE DRAWINGS

The construction of the apparatus of this invention, the methods of this invention, and the use of the apparatus and methods will be clarified by reference to the drawings.

Figure 1:
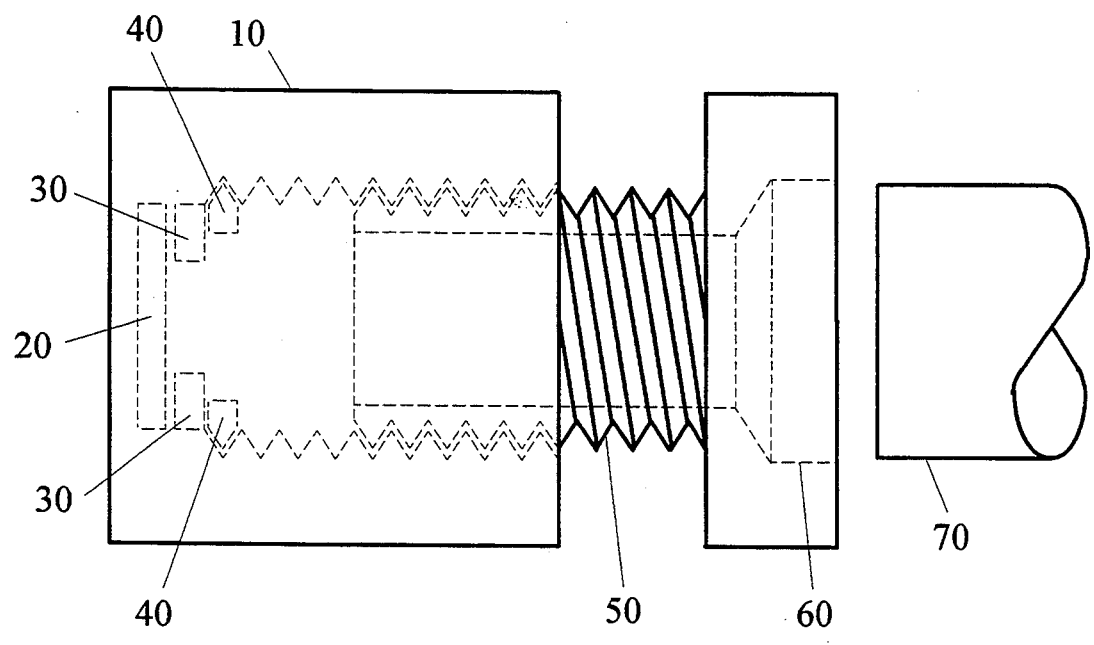
FIG. 1 shows an overall view of the simplest embodiment of the calibration standard apparatus.

FIG. 1 shows an overall view of a simple embodiment of the calibration apparatus. FIG. 1 is an exterior view, with some of the interior details shown by dashed lines. Other details not shown in FIG. 1 will be shown more clearly in the other figures. In FIG. 1, a housing 10 encloses other pans of the apparatus. The standard target element 20 is mounted inside housing 10, with one side of the standard target element facing an opening through which both non-visible light and fluorescent light from the standard target element can pass. Also inside housing 10, an aperture 30 is mounted against the side of standard target element 20 facing the opening. A retaining ring 40 holds the standard target element 20 and aperture 30 in place. Engaging the opening in housing 10 is an adapter portion 60 of the apparatus, which adapts the calibration apparatus to fit the optical front end 70 of a fluorescence detector (not further shown) with which the calibration apparatus of this invention is used. The interior of housing 10 and a portion of the exterior of adapter portion 60 are shown threaded in FIG. 1 as an example of means for continuously adjusting the distance between the standard target element 20 and the optical front end 70 of the fluorescence detector when adapter portion 60 is connected to optical front end 70.

Once the distance is adjusted to a predetermined distance, the distance may be fixed by a set screw or locking nut (not shown in the figures). In normal practice, the distance adjustment is done once by the manufacturer when setting up the calibration apparatus, and locked in place. If necessary, the locking mechanism such as a set screw or locking nut may be sealed to prevent re-adjustment of the distance by users. The predetermined distance to which the apparatus is adjusted is one which makes the area of the standard target element 20 that is exposed through aperture 30 subtend a desired solid angle as viewed from the optical front end 70 of the fluorescence detector, to produce a desired predetermined intensity of fluorescence light at the detector.

Figure 2:
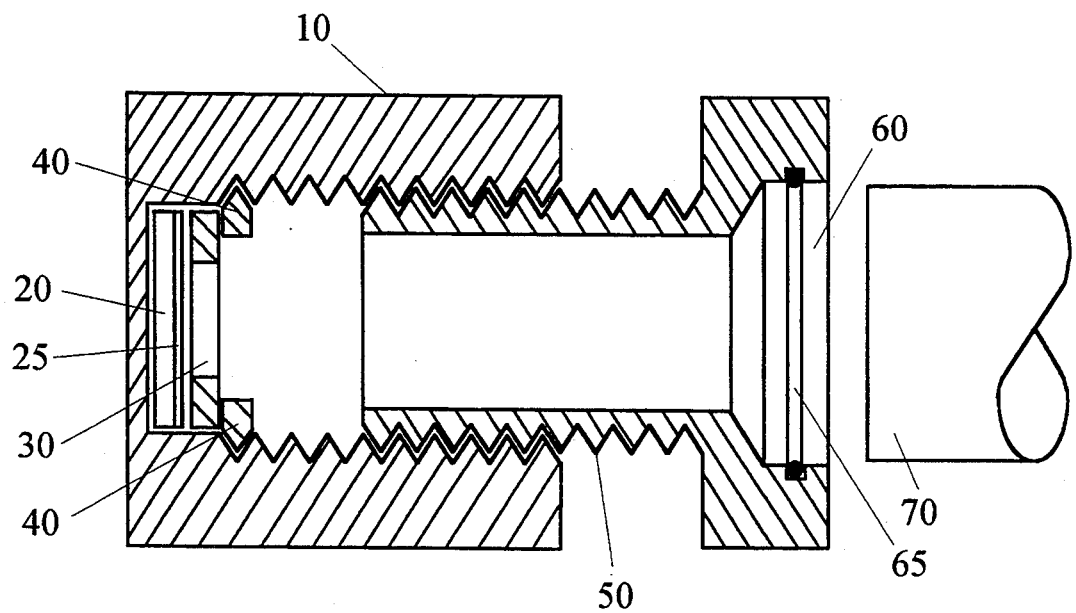
FIG. 2 is a cross-sectional view of the embodiment shown in FIG. 1, showing additional details.

FIG. 2 shows a cross-section of the same simple embodiment showing further details of the apparatus. It will be appreciated that a threaded coupling is but one of many ways that the relative distance between the standard target element 20 and the optical front end 70 may be adjusted. In other embodiments, the mutually movable parts might have a sliding fit and be secured in place by cement when the desired distance adjustment is achieved.

In FIG. 2, the standard target element 20 is shown with a transparent coating 25. This coating, if required to protect the surface of standard target element 20, must be both substantially transparent to the non-visible light used to excite fluorescence, and transparent to the fluorescence light itself. For some materials from which the standard target element 20 is fabricated, no coating 25 is needed. Coating 25 may be made of a non-fluorescent transparent plastic or of some glasses for example. The coating 25 is made preferably of quartz, which is transparent in the ranges of the visible spectrum and the ultra-violet spectrum, and presents a hard surface resistant to wear. If made of quartz, the coating 25 may be applied by sputtering quartz.

In FIG. 2, retaining ring 40 is shown as a threaded ring. In alternate embodiments, retaining ring 40 can instead be a split ring retainer or other retainer means.

In FIG. 2, the adapter end 60 of the apparatus is shown with an O-ring 65, as a simple example of flexible means of temporarily securing the calibration apparatus to the optical front end 70. O-ring 65 is made of a resilient polymeric material suitably dimensioned to fit over the outer diameter of the optical front end 70 of the fluorescence detector to be calibrated. Other preferred means of coupling the apparatus are shown below in discussion of details of a preferred embodiment.

Figure 3:
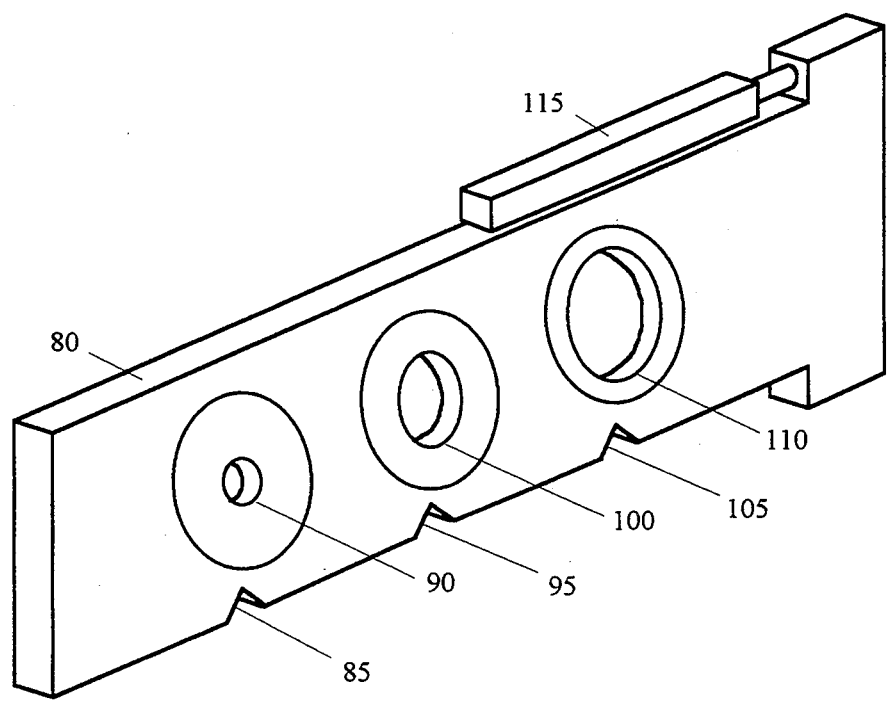
FIG. 3 shows in perspective view a detail of another embodiment of the calibration standard apparatus.

FIG. 3 shows a detail of another embodiment of the invention, in which several different standard target elements and/or several different apertures may be incorporated into the apparatus by using a sliding member 80. The sliding member 80 fits in a slot (not shown) in housing 10. Specifically shown in FIG. 3 are three portions 90, 100, and 110, each of which is an integrated combination of a standard target element 20 (with or without coating 25), and an aperture 30. The user of the apparatus can slide the appropriate target combination 90, 100, or 110 into an active position facing the fluorescence detector for different calibration situations. For example, for one type of calibration, the target combination 90 is prepared for the minimum detection specification of the fluorescence detector, target combination 100 is prepared for the average or typical detection specification, and target combination 110 is prepared for the maximum detection specification. Alternatively, the apparatus can have a single fixed aperture 30, and the portions 90, 100, and 110 can be standard target elements differing in composition with respect to the type or concentrations of fluorescent substance incorporated in them. Or, in another alternative arrangement, one standard calibration element may be mounted to housing 10 in a suitable fixed position and the sliding member 80 can carry various apertures of predetermined sizes, represented by portions 90, 100, and 110 for that alternative embodiment. For all of these embodiments, sliding member 80 has detent notches 85, 95 and 105 which provide for stable and reproducible positioning of the selected portions 90, 100, or 110 respectively at the active position in the housing, facing the fluorescence detector.

Thus multiple standard target elements can be substituted individually into the apparatus with each carried by one slide member 80, or all may be carried together on a single carrier such as slide member 80 of FIG. 3 and indexed to present each standard target element in turn.

Figure 4:
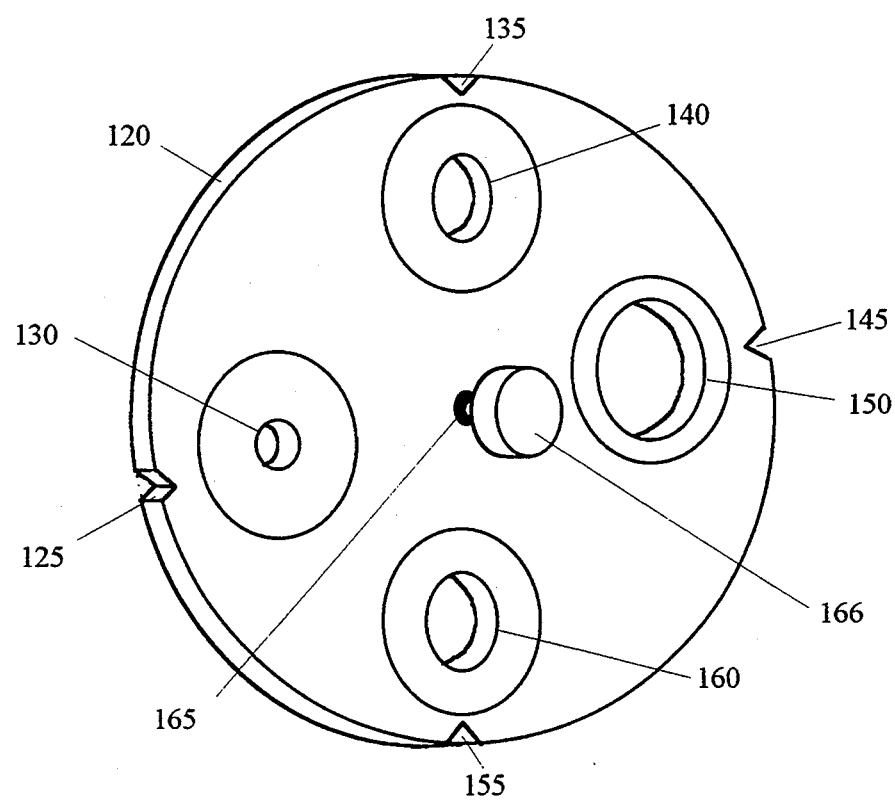
FIG. 4 shows in perspective view a detail of an alternate embodiment of the calibration standard.

FIG. 4 shows another alternative embodiment analogous to FIG. 3. In FIG. 4, a wheel 120 performs the same function as the sliding member 80 of FIG. 3. Wheel 120 carries the various portions 130, 140, 150 and 160, which again may be either standard target elements differing in composition, or apertures differing in diameter, or integrated combinations of standard target elements and apertures. Wheel 120 is rotated about its axis 165 to bring the appropriate portions 130, 140, 150, or 160 into play for a particular calibration situation. The detent notches 125, 135, 145 and 155 provide for stable and reproducible positioning of the selected portions 130, 140, 150, or 160 respectively at the active position in the housing, facing the fluorescence detector.

Either the sliding member 80 of FIG. 3 or the wheel of FIG. 4 may be operated by hand by the user of the calibration apparatus, or may be operated by an actuator, such as a spring 180, an electric motor 166, an ultrasonic motor, a piezoelectric linear actuator 115 or other mechanical aid.

Figure 5:
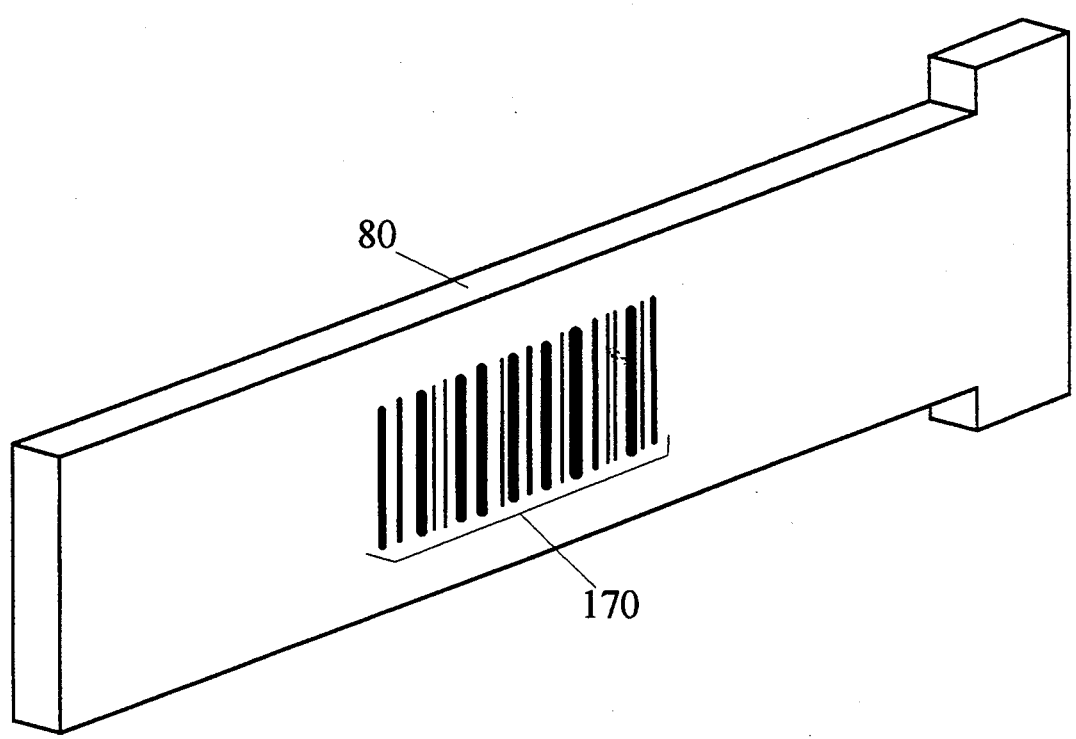
FIG. 5 shows in perspective view a detail of another alternate embodiment of the calibration standard.

FIG. 5 shows a detail of another embodiment of the calibration standard which is useful for calibration of fluorescence detectors requiring a dynamic calibration rather than a static calibration, such as in calibration of fluorescent bar code scanners. A slide 80 in FIG. 5 carries a standard target element 170, an example of a specific type of the standard target element 20 of FIG. 1. The element 170 in FIG. 5 is shown as a bar code, but may be any indicia or pattern of fluorescent and non-fluorescent substances intended to be read using a fluorescence detector. The purpose of slide 80 is to carry the standard target element, moving it from a starting position in housing 10 in a predetermined time to an ending position during a dynamic calibration. In the case of a bar code reader, the purpose of the movement is to simulate the motion of an article as it would occur in the application of checking bar-code identified articles. For the dynamic type of calibration, the calibration apparatus of this invention includes means of moving the standard target element and returning it to its starting position. The movement is preferably made parallel to the standard target element and perpendicular to the axis of the calibration apparatus, which lies in the plane of drawing FIGS. 1 and 2.

Figure 6:
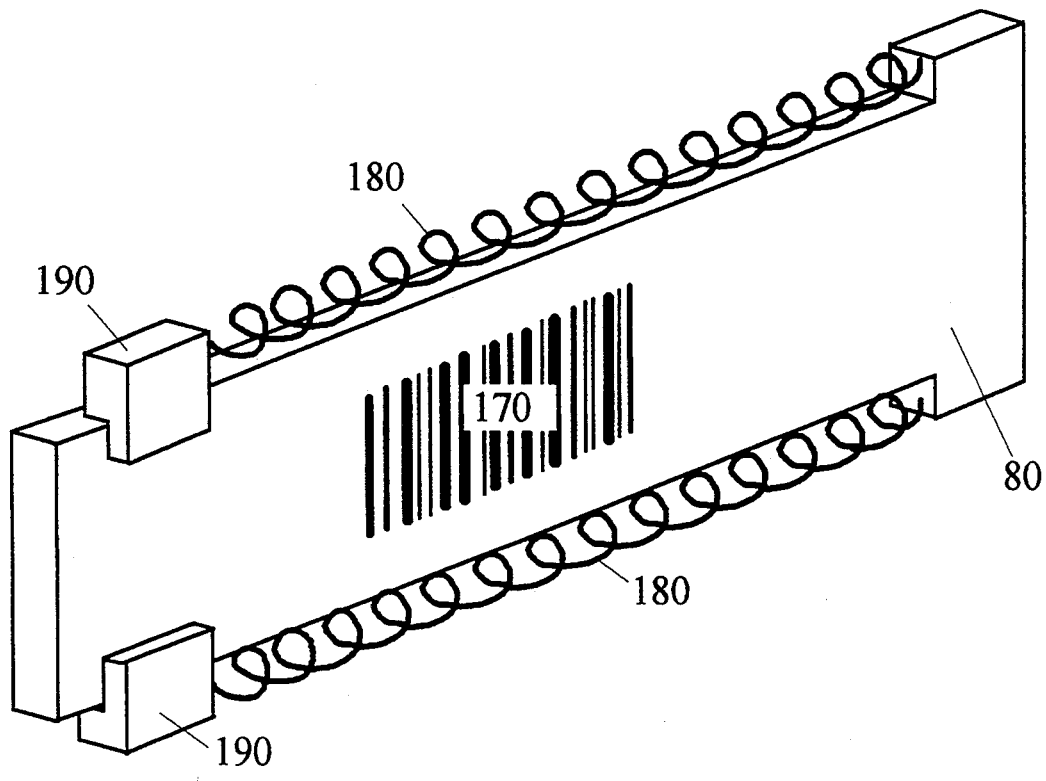
FIG. 6 shows in perspective view an example of a mechanism used with the embodiment of FIG. 5.

Very simple means of moving the standard target element within the calibration apparatus are shown in FIG. 6. FIG. 6 shows a slide 80 carrying indicia 170, such as the bar code shown in the figure. Springs 180 on both edges of slide 80 act to move slide 80, when slide 80 is released from a detent or latched position (not shown). Springs 180 are fixed to bosses 190, which are in turn fixed to housing 10. In FIG. 6, the bosses 190 also serve to guide slide 80 as it moves. The springs are preferably used to move slide 80 during the dynamic calibration to provide a reproducible time for transit from a first position to a second position. In this simple embodiment, slide 80 can be returned by hand to its first position by the operator of the calibration apparatus. In a more mechanized embodiment of the invention, the movement of slide 80 is accomplished by a motor 166, linear actuator 115, relay, or other mechanical aid. Similarly, other embodiments use a wheel, like wheel 120 of FIG. 4, instead of slide 80 of FIG. 5 to move the standard target element for dynamic calibrations. Slide 80 of FIGS. 5 and 6, or a wheel equivalent as in FIG. 4, can have detent notches like notch 85 or notch 125 to provide stable, reproducible starting and ending points of the movement, and can have ratchet elements (not shown) to latch the dynamic standard target element at a starting position when not being moved for a dynamic calibration.

Figure 7:
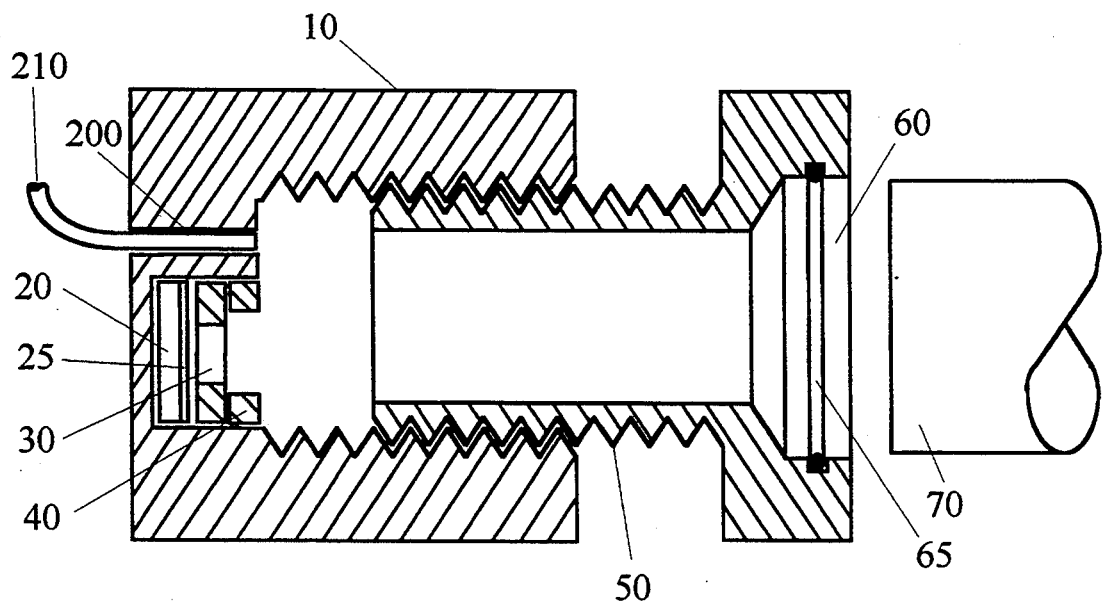
FIG. 7 shows a cross sectional view of an alternate embodiment.

FIG. 7 shows an embodiment of the calibration apparatus incorporating an additional feature useful for calibrating some fluorescence detectors. In FIG. 7, an additional input port 200 allows additional light to be selectively introduced into housing 10 to simulate during calibration the ambient light environment in which the fluorescence detector is to be used. Input port 200 is preferably a fiber-optic input connector accepting an optical fiber 210, which carries the additional light into housing 10. Input port 200 may be disposed to direct the additional light directly toward the fluorescent detector's optical front end 70 as shown, or alternatively may be disposed to illuminate the standard target element 20 and/or other portions of the interior of housing 10. In the latter case the additional light introduced through input port 200 reaches the fluorescent detector by reflection or scattering which may more realistically simulate the ambient lighting situation for some applications.

Figure 8:
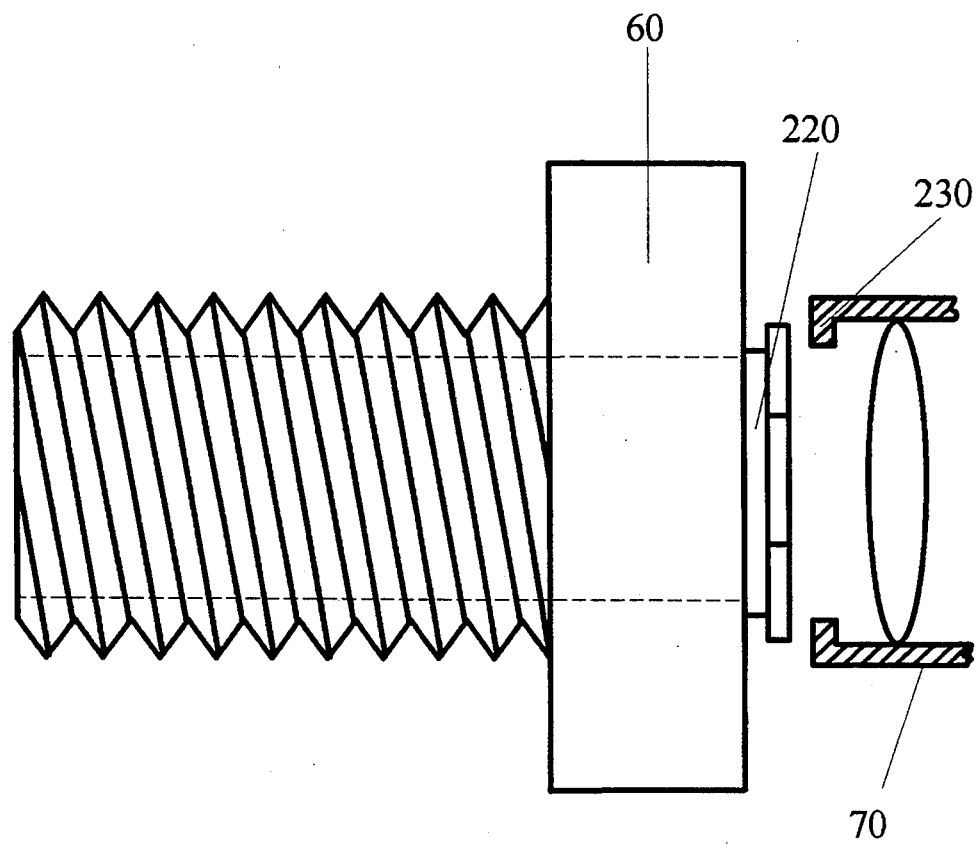
FIG. 8 shows a detail of a preferred embodiment of the calibration standard apparatus.

FIG. 8 shows a detail of a preferred embodiment for the adapter portion 60 of the calibration apparatus. In a preferred embodiment, a bayonet-type coupling member 220 is used on adapter portion 60, mating with corresponding bayonet-type coupling member 230, attached to or integral with the optical front end 70 of the fluorescence detector with which the calibration apparatus is to be used. A quick-coupling connector or adapter such as elements 220 and 230 allows the calibration apparatus of this invention to be used with a variety of different fluorescence detector models and provides for easy use during calibration.

The use of the calibration apparatus and of the methods of this invention is straightforward. When detection specifications for a fluorescence detector are established by a manufacturer, those specifications are translated into a standard target element for either static or dynamic calibration, depending on the application of the fluorescence detector. The specifications may require a set of standard target elements to calibrate to more than one specification. For example, the set can include a low calibration standard element and a high calibration standard element to cover the range of detection intensities of a detector. The user attaches the pre-set calibration standard to the fluorescence detector and makes a fluorescence reading for each calibration condition using the appropriate standard target element, and adjusts the fluorescence detector output to match the correct calibration. The procedure is the same for dynamic calibration, which, in the simplest embodiments of the calibration apparatus, require the user to initiate movement of the dynamic standard target element. In more mechanized versions of the invention, the target element movement for dynamic calibration is automated.

While the calibration apparatus and methods have been described above by reference to particularly simple embodiments for clarity, it will be apparent that other embodiments can be made that fall within the scope of this invention as claimed below.

I claim:

1. An apparatus for calibration of fluorescence detectors using non-visible light, comprising
   a) a housing impervious both to said non-visible light and to said fluorescence to be detected, having at least one opening means to admit passage of said non-visible light and of said fluorescence,
   b) a standard target element enclosed within said housing, comprising
      a predetermined combination of one or more predetermined fluorescent substances with one or more other substances,
   c) an aperture element enclosed within said housing and disposed between said
      standard target element and said at at least one opening means,
   d) adapting means for adapting said housing to fit a fluorescence detector, and
   e) means for adjusting the distance between said adapting means and said
      standard target element, so that a predetermined intensity of said fluorescence is presented to a detector to be calibrated.

2. An apparatus for calibration of fluorescence detectors as in claim 1, further comprising one or more means to move said standard target element from a first position in said housing by a predetermined distance in a predetermined time to a second position in said housing, and one or more means to return said standard target element to said first position.

3. An apparatus for calibration of fluorescence detectors as in claim 2, wherein said one or more means to move and said one or more means to return comprise one or more springs.

4. An apparatus for calibration of fluorescence detectors as in claim 2, wherein said one or more means to move and said one or more means to return comprise one or more linear actuators.

5. An apparatus for calibration of fluorescence detectors as in claim 2, wherein said one or more means to move and said one or more means to return comprise one or more electric motors.

6. An apparatus for calibration of fluorescence detectors as in claim 1, wherein said predetermined combination comprises a mixture of said substances.

7. An apparatus for calibration of fluorescence detectors as in claim 1, wherein said predetermined combination comprises a predetermined pattern of said fluorescent substance disposed on a background of said other substances.

8. An apparatus for calibration of fluorescence detectors as in claim 7, wherein said predetermined pattern comprises one or more bar codes.

9. An apparatus for calibration of fluorescence detectors as in claim 7, wherein said predetermined pattern comprises one or more straight lines.

10. An apparatus for calibration of fluorescence detectors as in claim 1, wherein said predetermined combination comprises a predetermined pattern of said other substances disposed on a background of said fluorescent substance.

11. An apparatus for calibration of fluorescence detectors as in claim 10, wherein said predetermined pattern comprises one or more bar codes.

12. An apparatus for calibration of fluorescence detectors as in claim 10, wherein said predetermined pattern comprises one or more straight lines.

13. An apparatus for calibration of fluorescence detectors as in claim 1, wherein said aperture element comprises a plate characterized by being opaque to said non-visible light and said fluorescence except in one or more transparent portions of predetermined size, shape and position.

14. An apparatus for calibration of fluorescence detectors as in claim 13, wherein said plate comprises an opaque disk with a round central portion transparent to said non-visible light and to said fluorescence.

15. An apparatus for calibration of fluorescence detectors as in claim 1, wherein said predetermined combination in said standard target element comprises a flat plate slidably mounted in said housing, said flat plate comprising one or more discrete portions containing one or more predetermined amounts of said fluorescent substances.

16. An apparatus for calibration of fluorescence detectors as in claim 1, wherein said predetermined combination in said standard target element comprises a disk rotatably mounted in said housing, said disk comprising one or more discrete portions containing one or more predetermined amounts of said fluorescent substances.

17. An apparatus for calibration of fluorescence detectors as in claim 1, wherein said means for adjusting distance comprises matching male and female threaded portions of said adapting means and said housing.

18. An apparatus for calibration of fluorescence detectors as in claim 1, wherein said adapting means comprise quick-disconnect coupling elements attaching said housing to said fluorescence detector.

19. An apparatus for calibration of fluorescence detectors as in claim 1, wherein said adapting means comprise bayonet-type coupling elements attaching said housing to said fluorescence detector.

20. An apparatus for calibration of fluorescence detectors as in claim 1, wherein said housing has an outer surface, an interior volume, and a bore defined by an inner surface having an inner diameter, said bore extending from said outer surface to said interior volume to admit light in addition to said non-visible light and said fluorescence into said interior volume of said housing.

21. An apparatus for calibration of fluorescence detectors as in claim 20, wherein said inner diameter of said bore is adapted to fit a transparent window admitting the additional light into said interior volume of said housing.

22. An apparatus for calibration of fluorescence detectors as in claim 20, wherein said inner diameter of said bore is adapted to fit a fiber-optic connector, thereby allowing light transmission by fiber optical means into said interior volume of said housing.

23. An apparatus for calibration of fluorescence detectors as in claim 1, wherein said standard target element has at least one side facing said at least one opening means, and said other substances comprise a coating transparent both to said non-visible light and to said fluorescence, covering at least said at least one side.

24. An apparatus for calibration of fluorescence detectors as in claim 23, wherein said coating comprises a layer of quartz.

25. A standard target element for calibration of fluorescence detectors using non-visible light, comprising a predetermined combination of one or more predetermined fluorescent substances with one or more other substances in fixed proportions, having at least one first side without said fluorescent substances, at least one second side with a predetermined fixed surface area of said combination of substances to be exposed to said detectors during calibration, said combination comprising a first fluorescent substance arranged in a predetermined pattern on a background comprising one or more substances selected from a group consisting of a nonfluorescent substance and a second fluorescent substance having a fluorescent emission spectrum differing from that of said fluorescent substance.

26. A standard target element for calibration of fluorescence detectors as in claim 25, wherein at least said second side is covered with a coating transparent both to said non-visible radiation and to the fluorescence of said one or more predetermined fluorescent substances, and said predetermined pattern comprises one or more bar codes.

27. A standard target element for calibration of fluorescence detectors as in claim 25, wherein said other substances comprise plastic substances.

28. A method for calibrating fluorescence detectors, comprising the steps of
 a) preparing a standard target element by the substeps of
  i) mixing a predetermined amount of a predetermined first fluorescent substance having a first fluorescent emission spectrum with one or more substances selected from the group consisting of
   A) a non-fluorescent substance and
   B) a second fluorescent substance having a second fluorescent emission spectrum differing from said first fluorescent emission spectrum and
  ii) if desired, covering the resultant mixture with material transparent both to non-visible light and to said first fluorescent emission spectrum to complete the preparation of said standard target element, and
 b) covering a first portion of said standard target element to expose a second portion having a predetermined area,
 c) adjusting the distance between said standard target element and a fluorescence detector to a predetermined distance,
 d) illuminating the exposed second portion of said standard target element with said non-visible light,
 e) measuring the response of said fluorescence detector to fluorescence from said standard target element, and
 f) adjusting said fluorescence detector response to equal a predetermined value, thus achieving the detector calibration.

29. A calibration method as in claim 28, wherein the step of preparing said standard target element includes an additional substep of arranging said first fluorescent substance into a predetermined pattern.

30. A calibration method as in claim 29, wherein said predetermined pattern comprises one or more bar codes.

31. A calibration method as in claim 29, wherein said predetermined pattern comprises one or more straight lines.

32. A calibration method as in claim 28, wherein the step (d) of illuminating said standard target element with said non-visible light is accompanied by the simultaneous substep of moving said standard target element from a predetermined first position to a predetermined second position in a predetermined time.

33. A method for preparing a standard target element for calibrating fluorescence detectors, comprising the steps of
 a) combining a predetermined amount of a predetermined first fluorescent substance having a first fluorescent emission spectrum with one or more substances selected from the group consisting of
  A) a non-fluorescent substance and
  B) a second fluorescent substance having a second fluorescent emission spectrum differing from said first fluorescent emission spectrum, in a mixture,
 b) forming the resultant mixture into a predetermined shape having at least one first side,
 c) if desired, covering said first side of said shape with material transparent both to non-visible light and to said first fluorescent emission spectrum, and
 d) covering a first portion of said first side to expose a second portion having a predetermined area, to complete the preparation of said standard target element.

34. A method for preparing a standard target element for calibrating fluorescence detectors, comprising the steps of
 a) arranging a predetermined amount of a predetermined first fluorescent substance having a first fluorescent emission spectrum into a predetermined pattern on a background comprising one or more substances selected from the group consisting of
  A) a non-fluorescent substance and B) a second fluorescent substance having a second fluorescent emission spectrum differing from said first fluorescent emission spectrum, b) forming the resultant patterned combination into a predetermined shape having at least one first side including said pattern, c) if desired, covering at least said first side of said shape with material transparent both to non-visible light and to said first fluorescent emission spectrum, and d) covering a first portion of said first side to expose a second portion having a predetermined area, to complete the preparation of said standard target element.

* * * * *